United States Patent
Devidas et al.

(10) Patent No.: US 7,556,785 B2
(45) Date of Patent: Jul. 7, 2009

(54) APPARATUS AND METHOD FOR RAPID AND CONTINUOUS GENERATION OF PHOSPHINE GAS

(75) Inventors: Shroff Rajnikant Devidas, Mumbai (IN); Pushpaksen P. Asher, Gujarat (IN)

(73) Assignee: United Phosphorus, Ltd., Mumbai (IN)

( * ) Notice: Subject to any disclaimer, the term of this patent is extended or adjusted under 35 U.S.C. 154(b) by 0 days.

(21) Appl. No.: 10/435,680

(22) Filed: May 12, 2003

(65) Prior Publication Data

US 2004/0228757 A1 Nov. 18, 2004

(51) Int. Cl.
| | |
|---|---|
| B01J 19/00 | (2006.01) |
| A62B 7/08 | (2006.01) |
| B01J 35/02 | (2006.01) |
| B01J 3/00 | (2006.01) |
| A61L 2/00 | (2006.01) |
| A61L 9/00 | (2006.01) |
| C01B 25/00 | (2006.01) |
| B01F 13/02 | (2006.01) |
| B01D 21/26 | (2006.01) |
| F15C 1/16 | (2006.01) |
| B01D 45/12 | (2006.01) |
| B01D 19/00 | (2006.01) |

(52) U.S. Cl. .............................. 422/305; 422/1; 422/28; 422/33; 422/123; 422/124; 422/211; 422/242; 422/231; 422/261; 422/292; 422/300; 422/306; 423/299; 366/106; 366/107; 210/304; 210/512.1; 137/812; 137/247.31; 55/349; 55/459.1; 95/271; 96/171; 96/209; 96/313; 96/321; 43/1; 43/124; 43/125

(58) Field of Classification Search .................... 422/1, 422/28–33, 40, 123–124, 211, 224, 231, 422/261, 292, 300, 305, 306; 423/299; 366/106–107; 210/304, 512.1; 137/812, 247.31; 55/349, 55/459.1; 95/271; 96/171, 209, 313, 321; 43/1, 124–125

See application file for complete search history.

(56) References Cited

U.S. PATENT DOCUMENTS

| | | | |
|---|---|---|---|
| 4,595,296 A | * | 6/1986 | Parks .......................... 366/106 |
| 4,651,463 A | * | 3/1987 | Friemel ........................ 43/125 |
| 4,814,154 A | | 3/1989 | Doernemann |
| 4,966,755 A | | 10/1990 | Smith |

(Continued)

FOREIGN PATENT DOCUMENTS

JP 08010568 A * 1/1996

(Continued)

Primary Examiner—Jill Warden
Assistant Examiner—Monzer R Chorbaji
(74) Attorney, Agent, or Firm—Jones, Tullar & Cooper, PC

(57) ABSTRACT

Phosphine gas is generated by agitating a reaction mixture of a metal phosphide and water with agitation air in a reaction pot of a phosphine gas generator. The resulting phosphine gas is then diluted with dilution air to produce a fumigant phosphine gas which is directly delivered to a commodity for fumigation. The reaction pot does not have any rotating means such as agitators, rotors, or stirrers. The generator provides on-site generation of phosphine gas in a rapid manner improving the fumigation efficiency for a commodity, such as grain, preferably contained within a storage structures, such as a grain silo. The generator has a built in deactivation system for the unused metal phosphide and phosphine gas.

13 Claims, 3 Drawing Sheets

U.S. PATENT DOCUMENTS

| | | | |
|---|---|---|---|
| 5,055,204 A * | 10/1991 | Bogart | 210/758 |
| 5,078,881 A * | 1/1992 | Augustine et al. | 210/602 |
| 5,260,022 A * | 11/1993 | Schellhaas et al. | 422/29 |
| 5,573,740 A * | 11/1996 | Banks et al. | 423/299 |
| 5,897,841 A | 4/1999 | Shroff | |
| 6,315,965 B1 | 11/2001 | Horn Feja et al. | |
| 6,383,413 B1 * | 5/2002 | Horn | 252/372 |
| 6,655,829 B1 * | 12/2003 | Vanden Bussche et al. | 366/165.1 |

FOREIGN PATENT DOCUMENTS

| | | |
|---|---|---|
| WO | WO 93/25075 | 12/1993 |

* cited by examiner

APPARATUS AND METHOD FOR RAPID AND CONTINUOUS GENERATION OF PHOSPHINE GAS

BACKGROUND OF THE INVENTION

1. Field of the Invention

The present invention is broadly related to a generator and a corresponding method for fumigating a commodity with a phosphine gas. Phosphine gas is generated by mixing a metal phosphide and water upon agitation and dilution with air.

2. Description of Related Art

Fumigation of stored agricultural commodities such as grains with phosphine gas is the foremost method of preventing insect damage. Typically, fumigation is achieved by introducing pellets or tablets containing metal phosphide directly into the grain to be fumigated. The metal phosphide reacts with the ambient moisture in the air and grain, resulting in the generation of a phosphine gas and other inert gases. Forced air circulation devices are often used to assist in distribution of the phosphine gas throughout a storage structure, such as a grain silo.

A common fumigation problem encountered with prior practices is the inability to achieve a uniform concentration of phosphine gas within the storage structure quickly. It is known that for the most effective insect control, it is necessary to maintain the desired concentrations of phosphine for known periods. However, with prior methods the release of phosphine gas is slow and takes three to seven days or more depending on the ambient conditions.

Batch processes for the generation of phosphine gas have been proposed in the past. Such batch processes include a batch reactor for the hydrolysis of metal phosphides to obtain phosphine gas, the latter being stored in closed cylinders. Such containers can then be used on-site to deliver phosphine gas at a specific concentration throughout a selected period of fumigation. A significant drawback of this technique is that one must store the phosphine gas in pressure vessels with subsequent delivery of the vessels to the storage structure. This results in a need for expensive cylinders and poses handling hazards. Also, the phosphine gas must be transported to the fumigation site.

A very common fumigation problem encountered with prior practices is the use of $CO_2$, $N_2$, argon, and other similar gases which aim to dilute the phosphine gas concentration and to maintain low levels of phosphine gas until the phosphine gas reaches the storage structure for fumigation. At the same time, prior practices require an increased inventory and additional handling and hazards of pressurized cylinders.

Prior methods and devices for generating phosphine gas using metal phosphide have a number of additional problems. First, any unreacted metal phosphide in the reaction mixture would remain in the commodity after fumigation. Therefore, the metal phosphide had to be withdrawn in the form of a fine powder or collected in a bag. This handling of the unreacted phosphide metal poses increased health concerns to the operator. Second, the temperature of the reaction pot would increase during the reaction, since the reaction is exothermic. Hence, cooling jackets were needed around the reaction pot which increases the cost of generating the phosphine gas.

There is accordingly a need in the art for an improved apparatus and method allowing the safe, rapid production of phosphine gas for on-site generation. The desired apparatus and method would produce the desired phosphine gas concentration for fumigation while avoiding the need to produce phosphine gas at a remote site using intermediate containers of phosphine gas. Also, an apparatus that generated phosphine gas on a continuous basis without the addition of rotating parts like agitators, stirrers and rotors would be advantageous. Additionally, any improved apparatus or method would reduce or eliminate any hazards associated with the prior methods, including eliminated the usage of inert gases.

BRIEF SUMMARY OF INVENTION

The present invention is broadly related to a generator and a corresponding method for fumigating a commodity, such as grain, with a phosphine gas. The generator and corresponding method are used to generate phosphine gas from a metal phosphide, preferably aluminum phosphide, magnesium phosphide and other similar phosphides. The generator and corresponding method produce phosphine gas in a rapid manner to attain a uniform peak concentration of phosphine gas in a very short period of time. The generator enables on-site generation of phosphine gas directly to an adjacent storage structure or commodity so that phosphine gas is directly delivered to the commodity or into the storage structure without intermediate storage in containers. Preferably, the generator is used to fumigate silos, stored grain, transport containers, and ships. The present method is directed to a rapid generation of phosphine gas, which ensures that the required amount of phosphine gas is released in a short interval of time of less than two hours. Hence, the problems associated with previous generators, wherein the initial concentration of phosphine gas is low and later builds up and subsequently declines, does not arise in the present generator.

The present invention overcomes the problems outlined above by providing a generator for the on-site generation of phosphine gas by directly delivering the phosphine gas to an adjacent commodity or storage structure as it is generated in a uniform manner. The generator preferably includes a mobile frame supporting a reaction pot. The reaction pot doesn't have any rotating parts like agitators, stirrers, and rotors and hence, there is no metal-to-metal friction, which leads to wear and tear. In the reaction pot, a metal phosphide and water are added to produce a reaction mixture which is agitated with air to produce a phosphine gas. The agitation of the reaction mixture is accomplished by passing air under pressure through the reaction pot. The air produces turbulence which agitates or stirs the reaction mixture. No additional inert gases are needed to carry the phosphine gas for fumigation. Additional air, preferably from a storage structure, is used to dilute the phosphine gas in the preferred range of 100 to 5000 ppm and this fumigant phosphine gas is directly delivered to the commodity to be fumigated. Since ambient air is preferably circulated within the reaction pot for agitation and dilution, the temperature within the reaction pot can easily be maintained at a temperature near 55° C.

The generator also preferably contains a deactivation system for removing any unused reaction mixture and/or phosphine gas. The deactivation system primarily includes a secondary reactor which is connected to various air compressors and blowers ensuring that the unused reaction mixture is free from any active metal phosphide. Any phosphine gas from the reaction pot or unreacted fumigant phosphine gas is also cleaned preferably using an absorption tank. This eliminates any handling hazards to persons involved in processing the commodity since the operator is not exposed to the unreacted metal phosphide.

Additionally, forced air circulation devices are used to evenly distribute the fumigant phosphine gas throughout the commodity to be fumigated. This greatly reduces the possibility of any localized increase in concentrate of phosphine gas which may lead to ignition or fire.

BRIEF DESCRIPTION OF THE DRAWING

The features and advantages of the present invention will become apparent from the following detailed description of a preferred embodiment thereof, taken in conjunction with the accompanying drawings, in which.

DETAILED DESCRIPTION OF THE INVENTION

Figure 1:
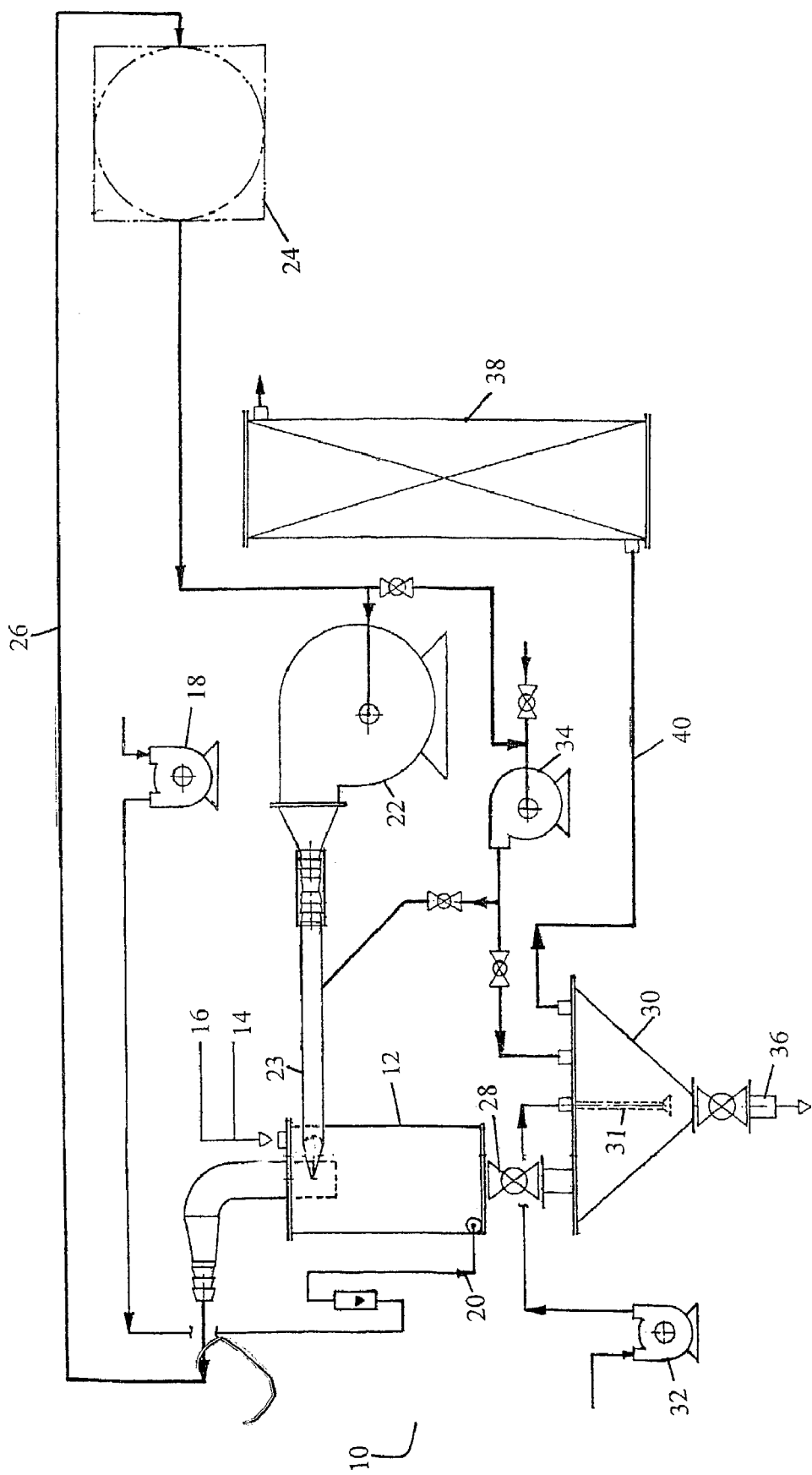
FIG. 1 is a flow diagram showing a preferred generator and method for making phosphine gas including a deactivation system containing a preferred secondary reactor and a preferred absorption tank.
Figure 2:
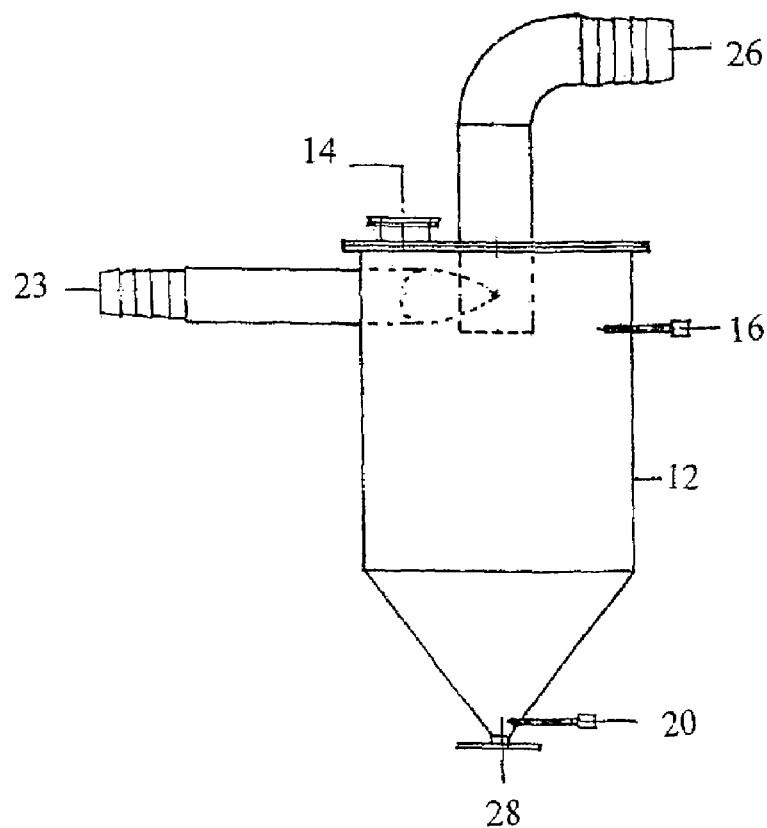
FIG. 2 is a side view of a preferred reaction pot.
Figure 3:
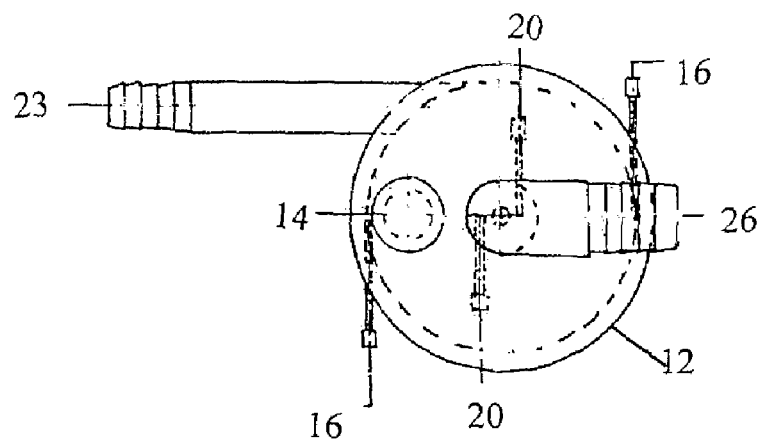
FIG. 3 is a top view of a preferred reaction pot.
Figure 4:
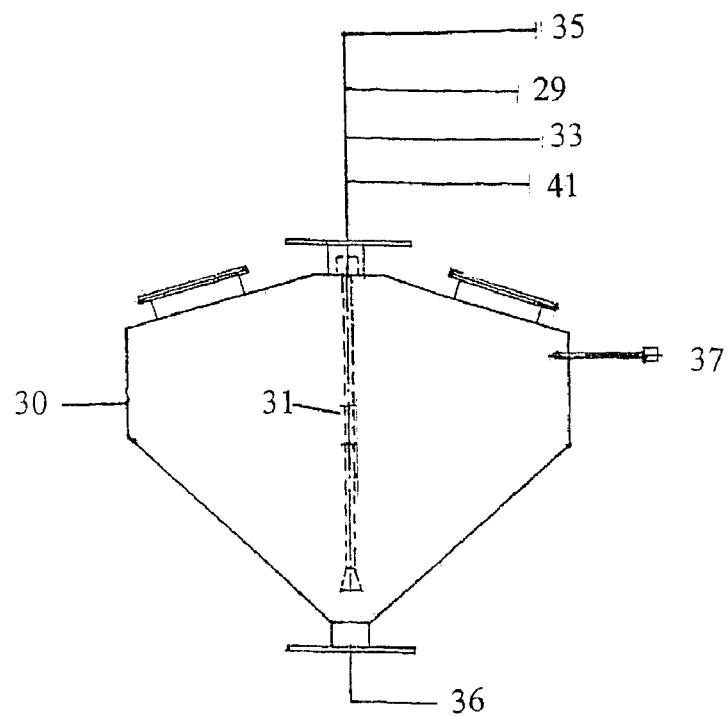
FIG. 4 is a side view of a preferred secondary reactor.
Figure 5:
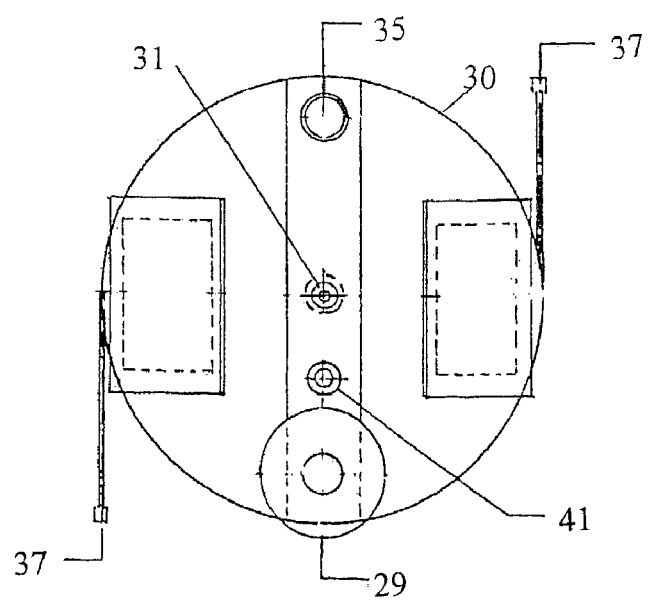
FIG. 5 is a top view of a preferred secondary reactor.

FIG. 1 shows the preferred generator 10 for generating a phosphine gas. The generator 10 contains a reaction pot 12 for generating the phosphine gas. The reaction pot 12 does not contain any rotating parts like agitators, stirrers, and rotors. Hence, there is no metal-to-metal friction which would lead to wear and tear of the reaction pot 12. A supply of a metal phosphide is fed to the reaction pot 12 via a metal phosphide input 14. The preferred metal phosphide is aluminum phosphide, magnesium phosphide and other similar phosphides. A supply of water is fed to the reaction pot via a reaction water input 16. Water and the metal phosphide are mixed in the reaction pot 12 to form a reaction mixture. In a preferred embodiment, 1 kg. phosphine gas is generated using 2.2 kg of 77.5% aluminum phosphide mixed with 10 liters of water. A supply of agitation air from an agitation air compressor 18 is fed to the reaction pot 12 via an agitation air input 20. As shown in the side view and the top view of the reaction pot 12, see FIG. 2 and FIG. 3, the agitation air input 20 provides a supply of agitation air to the reaction pot 12 via a tangential entry. In a preferred embodiment, a bottom portion of the reaction pot 12 is a conical shape where the supply of agitation air enters the reaction pot 12. The reaction mixture containing the metal phosphide and water react to generate a phosphine gas upon agitation with the agitation air. Preferably, the agitation air fed to the reaction pot 12 is ambient air such that the phosphine gas generated does not increase beyond 55° C. The agitation air from the agitation air compressor 18 is preferably supplied at a turbulating pressure of 0.5 to 2 kg/cm². The phosphine gas is then diluted by a supply of dilution air from a dilution blower 22 producing a fumigant phosphine gas. The dilution blower 22 is connected to the reaction pot 12 via a dilution air input 23. As shown in FIG. 2 and FIG. 3, the dilution air input 23 provides a supply of air to the reaction pot 12 via a tangential entry. Preferably, the dilution air is ambient air such that the fumigant phosphine gas does not exceed a temperature of 55° C. The fumigant phosphine gas in preferably diluted such that the amount of phosphine gas in the fumigant phosphine gas ranges from 100 to 5000 ppm. Preferably, the amount of dilution air added to the phosphine gas is such that the concentration of phosphine gas should not increase the auto ignition limit (1.8%) at STP. The fumigant phosphine gas is then directly delivered to a commodity 24 to be fumigated via fumigant line 26. The term "directly delivered" should be construed to mean that the fumigant phosphine gas is fed directly to the commodity without the need for intermediate storage containers or additional dilution means, such as inert gases. The commodity 24 is preferably disposed within a storage structure, such as a silo, transport container or ship. In a preferred embodiment, any fumigant phosphine gas that does not react with the commodity exits the commodity as unreacted fumigant phosphine gas. The unreacted fumigant phosphine gas may be recycled to the commodity 24 by directing a portion of the unreacted fumigant phosphine gas to the dilution blower 22. Alternatively, any unreacted fumigant phosphine gas may be cleaned as discussed below.

Once the commodity 24 has been fumigated, any unused reaction mixture and phosphine gas may be directed to a secondary reactor 30 for deactivation. Any unused reaction mixture and phosphine gas remaining in the reaction pot 12 are preferably discharged from the reaction pot 12 via an unused reaction mixture line 28 to the secondary reactor 30 at an unused reaction mixture inlet 29. The secondary reactor 30 contains an air sparger 31 which is connected to a residue compressor 32 via a sparger inlet 33. The secondary reactor 30 is also connected to a unreacted gas blower 34 which provides air and unreacted fumigant phosphine gas to the secondary reactor 30 via an unreacted gas inlet 35. Additionally, a supply of cleaning water is supplied to the secondary reactor 30 via at least one cleaning water inlet 37. The cleaning water may be used to scrub the unused reaction mixture and unreacted fumigant phosphine gas. The secondary reactor 30 produces a drainable residue that is free from any active metal phosphide. The drainable residue from the secondary reactor 30 is removed via residue outlet 36. The phosphine gas remaining in the secondary reactor 30 is fed to an absorption tank 38 via phosphine gas absorption line 40. Likewise, any unreacted fumigant phosphine gas may be cleaned by directing the unreacted fumigant phosphine gas from the commodity 24 to the residual collection tank 30 via the unreacted gas blower 34 and unreacted gas inlet 35. The secondary reactor 30 and absorption tank 38 provide any environmentally friendly means by which to clean the unused reaction mixture and phosphine gas after the commodity is fumigated. In a preferred embodiment, the deactivation process takes about 180 minutes. It should be understood that one of ordinary skill in the art may utilize other similar means for removing and/or cleaning the unused reaction mixture and phosphine gas from the generator 10.

Additionally, forced air circulation devices are preferably used to evenly distribute the fumigant phosphine gas throughout the commodity 24. This greatly reduces the possibility of any localized increase in concentrate of phosphine gas which may lead to ignition or fire.

The generator 10 produces phosphine gas having a uniform peak concentration in a short interval time, preferably less than two hours. This generation produces a maximum amount of phosphine gas and the reaction time of the phosphine gas with the commodity is very slow. The amount of phosphine gas released to the environment is negligible, preferably between 5-10 ppm. Phosphine gas can be generated in amount of from 0.56 gms to 10,000 Kg or higher. Multiple reaction pots 12 can be used to generate larger quantities of phosphine gas. Since, there is through passage for phosphine gas and the generator is completely closed, there is no leakage of the fumigant gas. There is no usage of inert gases to carry phosphine gas to the commodity or storage structure to be fumigated. One treatment of a grain silo is sufficient to completely kill the insects in the commodity. Also, the preferred generator has a battery back up and hence continues safe operation in the event of power failure. Preferably, the generator is a mobile unit.

EXAMPLE

An aluminum phosphide formulation, preferably containing 77.5% of the active ingredient, is used for phosphine gas generation for fumigation. The aluminum phosphide formulation contains 90% aluminum phosphide technical material, which contains a total of 86.2% active aluminum phosphide. The aluminum phosphide contains 10% paraffin wax having a melting point of 60-62° C. Other inert products like paraffin oil, at a different melting point, and petroleum jelly can also be used for dilution of the aluminum phosphide technical material. The aluminum phosphide formulation is in a granular form, hence safe to handle. There is no need to add additional diluents and/or ammonia to the formulation to reduce the active aluminum phosphide to make it safe for use as a fumigant Either the aluminum phosphide formulation is added to water or water is added to the aluminum phosphide formulation to generate phosphine gas in the reaction pot. A first source or air under pressure is used to stir the water and aluminum phosphide. A second source of air is used to dilute the phosphine gas generated from the reactor and to carry the resulting fumigant phosphine gas to the commodity for fumigation.

Although the present invention has been disclosed in terms of a preferred embodiment, it will be understood that numerous additional modifications and variations could be made thereto without departing from the scope of the invention as defined by the following claims.

What is claimed is:

1. A method for generating a fumigant phosphine gas comprising:
   a) providing a reaction pot;
   b) providing a pre-determined quantity of granular metal phosphide into the reaction pot;
   c) providing a predetermined quantity of water to the granular metal phosphide in the reaction pot to form a reaction mixture of granular metal phosphide and water;
   d) agitating the reaction mixture using a supply of air at a turbulating pressure of 0.5 to 2 $kg/cm^2$, wherein said supply of air is supplied tangentially to the reaction pot;
   e) generating a predetermined quantity of phosphine gas from 56 g to 10,000 g in less than two hours by agitating the reaction mixture, wherein the reaction temperature does not exceed 55° C.; and
   f) diluting the phosphine gas by supplying dilution air to the reaction pot thereby generating a fumigant phosphine gas, said dilution air is supplied tangentially to the reaction pot thereby producing a fumigant phosphine gas containing 100 to 5000 ppm phosphine gas.

2. The method of claim 1, wherein said step of diluting the phosphine gas includes providing a supply of ambient air only, without using any additional inert gas.

3. The method of claim 1, wherein said step of providing a supply of a granular metal phosphide into the reaction pot includes providing a supply of aluminum phosphide.

4. The method of claim 1, further comprising
   f) directly delivering said fumigant phosphine gas to a commodity.

5. The method of claim 4, further comprising
   g) recycling a supply of unreacted fumigant phosphine gas from said commodity with the supply of dilution air to said reaction pot.

6. The method of claim 4, wherein said step of directly delivering said fumigant gas to said commodity includes directly delivering said fumigant gas to a supply of commodity to be fumigated.

7. The method of claim 4, wherein the step of directly delivering said fumigant phosphine gas to the commodity includes directly delivering said fumigant gas to a silo, a transport container, or a ship containing said commodity.

8. The method of claim 1, wherein said granular metal phosphide includes at least 77.5% metal phosphide as the active ingredient.

9. The method of claim 1, wherein said step of providing a supply of air includes providing a supply of ambient air only, without using any additional inert gas.

10. The method of claim 1, wherein said step of providing a reaction pot includes providing a reaction pot with a bottom portion having a conical shape and said supply of air is provided to said reaction pot via tangential entry at said bottom portion.

11. The method of claim 1 further comprising a step of deactivating any unused reaction mixture, phosphine gas or a mixture thereof from the reaction pot using a provided deactivation system, wherein said deactivation system comprises at least a secondary reactor or an absorption tank.

12. A method for generating a fumigant phosphine gas comprising:
   a) providing a reaction pot having a reaction water input, an agitation air input, a metal phosphide input, a dilution air input, and a fumigant line, wherein each of said agitation air input, reaction water input and dilution air input are connected to the reaction pot to provide for tangential entry of material to the reaction pot, and wherein said agitation air input is connected to a bottom portion of the reaction pot, said bottom portion of the reaction pot having a conical shape;
   b) providing a pre-determined quantity of granular metal phosphide into the reaction pot;
   c) providing a pre-determined quantity of water into the reaction pot via the reaction water input;
   d) forming a reaction mixture of granular metal phosphide and water;
   e) providing a supply of air at a turbulating pressure of 0.5 to 2 $kg/cm^2$ to the reaction pot for agitating the reaction mixture at a reaction temperature not to exceed 55° C., said supply of air is supplied via the agitation air input;
   f) generating a uniform peak concentration of phosphine gas in an amount of from about 56 g to about 10,000 g from the reaction mixture in less than two hours from the adding of water to the granular metal phosphide;
   g) providing a supply of dilution air to the reaction pot to dilute the phosphine gas thereby producing a fumigant phosphine gas having 100-3000 ppm phosphine gas, said supply of dilution air is supplied via the dilution air input.

13. The method of claim 12 further comprising a step of deactivating any unused reaction mixture, phosphine gas or a mixture thereof from the reaction pot using a provided deactivation system, wherein said deactivation system comprises at least a secondary reactor or an absorption tank.

* * * * *